United States Patent [19]

Cowfer

[11] Patent Number: 4,760,207
[45] Date of Patent: Jul. 26, 1988

[54] RECOVERY OF ETHYLENE, CHLORINE AND HCL FROM VENTED WASTE GAS FROM DIRECT CHLORINATION REACTOR

[75] Inventor: Joseph A. Cowfer, Medina, Ohio

[73] Assignee: B.F. Goodrich Company, Akron, Ohio

[21] Appl. No.: 908,744

[22] Filed: Sep. 18, 1986

[51] Int. Cl.$^4$ .................... C07C 17/02; C07C 17/154; C07C 17/38

[52] U.S. Cl. .................... 570/243; 570/241; 570/245; 570/254; 570/262

[58] Field of Search ............... 570/243, 245, 241, 262, 570/254

[56] References Cited

U.S. PATENT DOCUMENTS 4,046,822 9/1977 Severino ........................... 570/241
4,590,317 5/1986 Linczyk ............................ 570/241

OTHER PUBLICATIONS

Lange, "Handbook of Chemistry" 10th Ed. (1961), pp. 256 and 257.

Primary Examiner—J. E. Evans

[57] ABSTRACT

In a process for producing 1,2-dichloroethane or ethylene dichloride ("EDC") in a high temperature direct chlorination ("HTDC") reactor in which ethylene is reacted with wet chlorine having a water content more than 100 ppm but no more than 1% by wt of the chlorine, the water leaves the reactor with the EDC product draw-off, either in the vapor overhead (if the HTDC is a boiling reactor), or, as a liquid sidestream (if the HTDC is a non-boiling reactor). In a subsequent step, the EDC draw-off is distilled in a product distillation column in which the water leaves in the overhead which is condensed to remove condensables in a first stage, and vent a non-condensable vent streams. The vent stream is corrosive due to the presence of minor amounts of chlorine, HCl and water, along with oxygen which is injected into the HTDC to improve selectivity of the reaction. The vent gases from the first stage are further cooled to a temperature in the range from about −30° C. to about 0° C. to condense condensables and freeze water without plugging the liquid lines. Plugging is avoided provided the vent stream contains less than 1.5% by wt of water, based on the weight of the vent stream. The essentially moisture-free non-condensables remaining are relatively non-corrosive and may be recycled to an oxychlorination reactor, also for the production of EDC, without unduly sacrificing the vent compressor and other carbon steel equipment in the recycle line.

5 Claims, 1 Drawing Sheet

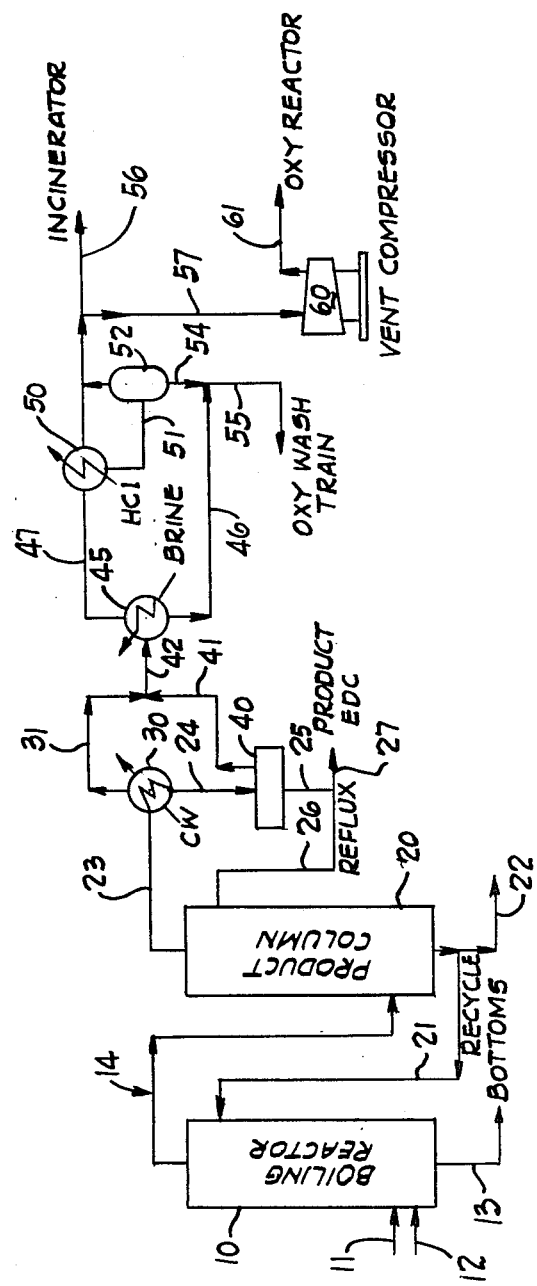

RECOVERY OF ETHYLENE, CHLORINE AND HCL FROM VENTED WASTE GAS FROM DIRECT CHLORINATION REACTOR

BACKGROUND OF THE INVENTION

The "direct chlorination of ethylene" is the basis for the widely used commercial catalytic process for the production of ethylene dichloride ("EDC", or 1,2-dichloroethane). The reaction is controlled by mass transfer, with absorption of ethylene as the limiting factor whether the reaction is carried out with a slight excess of ethylene, or as an alternative option (considerations relating to which are set forth hereinafter), a slight excess of chlorine, fed to the reactor. The heat of reaction is dissipated either through conventional water cooling of a typical low temperature direct chlorination reactor operating in the range from about 50° C. to about 65° C., or by operating the reactor at, or near, the boiling point of EDC under pressure up to about 200 psig, hence referred to as a "high temperature direct chlorination (HTDC) reactor". The HTDC reactor is a particular type of direct chlorination reactor. In one embodiment, referred to as a "boiling reactor" the HTDC is operated at the boiling point of EDC, and product EDC is drawn off as vapor; in another embodiment, referred to as a "non-boiling reactor", the HTDC is operated near the boiling point and product EDC is drawn off as a liquid sidestream.

The direct chlorination reaction may be written:

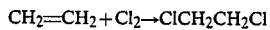

$$CH_2=CH_2+Cl_2\rightarrow ClCH_2CH_2Cl$$

and theoretically, neither water nor HCl is formed as a product of this reaction. In practice, in the presence of oxygen, some water may be formed in some side reactions, and some HCl is formed in another side reaction which may be written:

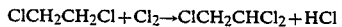

$$ClCH_2CH_2Cl+Cl_2\rightarrow ClCH_2CHCl_2+HCl$$

The precise amount of HCl formed depends upon the type of catalyst used in the HTDC reactor, the liquid medium in which the reaction is carried out (typically a chlorinated hydrocarbon such as EDC), and the conditions of reaction.

The direct chlorination process is desirably complemented by an oxychlorination ("oxy") process in which ethylene reacts with HCl and oxygen to produce EDC in an oxy reactor. This combination of direct chlorination and oxychlorination processes is referred to as "the balanced process" (for further details see the chapter titled "Vinyl Polymers (Vinyl Chloride)" by Cowfer, J. A. and Magistro, A. J, Encyclopedia of Chemical Technology, Kirk & Othmer, Vol 23, 865–885). In the flow-sheet therein, it was there suggested that crude EDC produced in the HTDC reactor be neutralized with alkali. The obvious economic burden of disposing of the neutralized material added to the cost of alkali, dictates that this be a less preferred solution.

It has long been known that the effluent from a HTDC reactor is highly corrosive. Recently it was found that the main cause of such corrosion is the presence of free chlorine and trace quantities, less than 100 parts per million (ppm), of water. A process for scavenging free chlorine in an EDC stream, to minimize the corrosion due to the chlorine, is disclosed in U.S. Pat. No. 4,547,599. This corrosion problem is aggravated when the chlorine feed to the boiling reactor is "wet", that is, contains at least 100 ppm of water, which, for example, is the case with gaseous chlorine from electrolytic cells. This problem also arises in a recycle line, including a vent compressor and related equipment, to the oxy reactor, when vent gases vented after recovery of product EDC, are recycled to the oxy reactor. It stands to reason that if there is no water being introduced in the feed to the HTDC reactor, and no water is generated in the direct chlorination reaction, there will be no water in the effluent from the reactor, and no corrosion problem to be solved.

As is well known, the economics of chemical engineering unit operations in the production of EDC are such that, optimally, the ethylene and chlorine are converted to EDC without the formation of unwanted byproducts and most important, without leaving any free chlorine in the effluent. The problem of corrosion is discussed in "Alloy Selection for VCM Plants" by Schillmoller, C. M., *Hydrocarbon Processing* pg 89–93, March 1979.

In practice, economics dictate that the direct chlorination reaction be controlled so that carbon steel equipment may be used. The problem is that free chlorine and water in carbon steel equipment and piping has a highly corrosive effect far more deleterious than either one or the other, and as little as from about 20 ppm to about 60 ppm of chlorine with trace amounts of moisture in the range from 10 ppm to about 50 ppm upstream of the EDC reactor, will destroy its tubes. The corrosion is exacerbated by the injection of oxygen into the direct chlorination reactor, for reasons set forth hereinfter.

For the foregoing reason, the only practical option is not to use an excess of chlorine in the reactor thus minimizing the amount of unreacted chlorine (referred to as "free" or "breakthrough" chlorine) leaving the reactor; instead, an excess of ethylene is supplied to the reactor. By "excess" ethylene I refer to an amount greater than that stoichiometrically required to produce the EDC, and typically from 1 to about 5% excess may be used, less than 2% excess being preferred. However, even when more than a 2% excess ethylene is supplied to minimize unreacted chlorine, the amount of free chlorine in the effluent remains in the range from about 100 ppm to about 3000 ppm, and substantially all of it has to be removed before the EDC is converted to VC monomer. It is economically onerous to use much more than a 2% excess of ethylene, but even doing so, then attempting to scavenge unreacted chlorine by injecting ethylene into the effluent, does not eliminate the chlorine. The excess ethylene used gets vented as a "vent stream" during recovery of product EDC and is recycled, usually to the oxychlorination reactor along with such moisture, chlorine and HCl as may be present.

The EDC is purified, then pyrolyzed in an EDC cracking furnace to produce vinyl chloride monomer ("VCM") in a reaction referred to as dehydrochlorination, the details of which are well known, and HCl generated in the furnace is recycled to the oxychlorination reactor.

The very small amounts of moisture, chlorine and HCl in the vent stream, each of which is present in relatively small amounts of the vent stream the major portion of which is ethylene and nitrogen, do not appear to be worth recovering because the cost of recovery due to severe corrosion problems, would outweigh the value of the recovered components. But the value of removing moisture to minimize corrosion of the equipment in the recycle line including equipment, to the oxy reactor, which value was never realized in the prior art, with the added value of ethylene and HCl recovered for recycle to the oxy reactor, justifies the cost of recovery.

In the prior art, the goal in a balanced process was the recovery and recycling of ethylene, chlorine and HCl in the effluent from any available source, whether direct chlorination reactor, condensers, storage tanks, and the like. And, as will readily be apparent if such a combined effluent is to be recovered for its chlorine, HCl and ethylene values, it is logical to recycle it to the oxy reactor. The major emphasis was on the recovery of ethylene which they used in large excess to minimize the amount of unreacted chlorine, and they appear to have been unconcerned with the effect of moisture on the materials of their equipment, as they did not dry the vent stream they recycled.

Such a process for the recovery of combined vent gases containing ethylene, chlorine, HCl and water, which gases are generated in an EDC plant, is disclosed in Offenlegungsschrift DE No. 3044854 A1 published July 1, 1982. The vent gases from a direct chlorination reactor operating at atmospheric pressure or above, are cooled to a temperature in the range from 1° to 2° C., but no cooler, so that the water in the vent gases does not freeze and plug up the lines. The vent gases which do not condense are then washed with water and alkali to remove unreacted chlorine. Clearly they had no intention of removing water, and of course, condensed only so much as the partial pressure of water in the vent stream would allow at a temperature above the freezing point of water.

The reference also teaches that attempts to remove a higher ratio of condensables by dropping the temperature to −20° C. were unsuccessful because the moisture present in the lines froze and plugged them. It was this discovery which led the German patentees to cool the vent gases to above the freezing point of water, and tolerate the smaller ratio of condensables including water, which they obtained at the higher condensing temperature since they were interested in recycling the combined vent stream to the oxychlorination reactor where the presence of additional moisture was not material. As is well known, an equimolar amount of water and EDC is generated in the oxychlorination reaction which may be written as follows:

$$CH_2=CH_2 + 2HCl + 0.5O_2 \rightarrow ClCH_2CH_2Cl + H_2O$$

For the patentees, water was not removed, and in the particular instance in the prior art referred to by the patentees, where the vent gases were chilled to the subfreezing temperature (of water), it is evident that the formation of ice (which plugged the lines and equipment) defeated the removal of water on a continuing basis. Thus, such separation as may have occurred was incidental or accidental and had nothing to do with minimizing the corrosion in the equipment due to the presence of water in the vent gases. Most of all, it may not have been realized that isolating the vent gases from the product column, avoided the problem of too much water in the combined vent gases from all over the EDC facility. Not coincidentally, the choice of the materials of construction of their recycle line and equipment appears to have been made to cope with the problem of corrosion due to the presence of the chlorine and moisture, both in the effluent line from the HTDC reactor, and in the recycle line to the oxy reactor.

SUMMARY OF THE INVENTION

It has been discovered that traces of water in the corrosive product draw-off from a direct chlorination reactor, may be removed in a subsequent step, from a product column vent stream in a facility for the production of EDC. The vent stream is chilled to a temperature below 0° C. without plugging the equipment and lines due to the formation of ice, provided the moisture content of wet chlorine feed to the HTDC reactor is less than 1% by wt of the chlorine, and the amount of water in the draw-off from the reactor is less than 300 ppm based on the total wt of the draw-off.

It is therefore a general object of this invention to provide a process for minimizing corrosion due to moisture in vent gases from a HTDC reactor, which vent gases are recycled to an oxychlorination reactor for the production of EDC, said process comprising, (a) reacting wet chlorine, having a moisture content in the range from 100 ppm to about 1% by weight of the chlorine fed, with an excess over stoichiometric of ethylene in a liquid chlorohydrocarbon medium at a temperature of at least about 50° C. at atmospheric pressure or above, to yield product EDC in a draw-off from the HTDC reactor, (b) separating product EDC from higher boiling components in the draw-off from the HTDC, in a vapor-liquid separating means such as a product distillation column, (c) condensing overhead from the distillation column into an overhead drum so as to condense the major portion of the EDC, and vent a stream consisting essentially of nitrogen, ethylene, chlorine, HCl and less than 1.5% by wt of water, based on the weight of the vent stream, (d) cooling the vent stream to a temperature in the range from about −30° C. to 0° C. to condense condensables in the vent stream and freeze water, (e) separating said water and condensables from non-condensables including nitrogen, chlorine, ethylene and HCl, without plugging lines with ice, and, (f) recycling said non-condensables essentially free of water to said oxychlorination reactor, whereby corrosion due to the presence of water in the recycle line and equipment is minimized.

BRIEF DESCRIPTION OF THE DRAWING

The foregoing and other objects and advantages of this invention will appear more fully from the following description, made in connectin with the accompanying drawing which schematically illustrates a preferred embodiment of the invention. The drawing is a simplified schematic flow diagram illustrating the relationship of a typical boiling reactor which is a particular embidment of a high temperature direct chlorination (HTDC) reactor, and a product column, and the flow of effluents from each, which flow results in a product column vent gas which is to be chilled, then compressed by a vent gas compresor for recycle to an oxy reactor.

DETAILED DESCRIPTION OF PREFERRED EMBODIMENTS

This invention is described in a particular embodiment, in relation to a HTDC reactor which is a boiling reactor, it being understood that the invention is equally applicable to any direct chlorination reactor in which the reaction of chlorine and ethylene produces a substantially pure (99.+%) EDC draw-off containing from about 100 ppm to about 0.5% by wt of chlorine, and relatively small amounts (relative to the volume of draw-off from the HTDC reactor), of nitrogen, HCl, ethylene, oxygen and water vapor. Typically, ethylene is in the range from about 500 ppm to about 1.0%; polychlorinated compounds are in the range from about 50 ppm to about 0.1%; HCl is in the range froom about 0.5% to about 7%; nitrogen is in the range from about 0.4% to about 20%; and oxygen is in the range from about 0.1% to about 5% by wt based on the combined components of the HTDC effluent, along with small amounts of carbon dioxide and ethane.

Referring to the drawing, there is shown a schematic flow diagram of a HTDC reactor indicated generally by reference numeral 10, in which liquid EDC and a catalytic amount of a direct chlorination catalyst such as $FeCl_3$, sufficient for the purpose, is held under elevated pressure from about 1 atm to about 3 atm, at its boiling point. A slight molar excess of ethylene, from about 1% to about 5% over the stoichiometric amount necessary to react with chlorine and form EDC, referred to herein as "excess ethylene", is fed through an ethylene feed line 11, and chlorine is fed through a chlorine feed line 12, both near the bottom, so that they react exothermically within hot liquid chlorinated hydrocarbons (chlorohydrocarbon "CHC" liquid), mainly EDC, held as the liquid reaction medium in the reactor.

The CHC liquid normally includes minor amounts of 1,1,2-trichloroethane ("triane"), 1,1,1,2- or 1,1,2,2-tetrachloroethane, and pentachloroethane, and other CHC impurities formed in the HTDC reactor due to side reactions.

The heat of reaction boils off EDC while the reaction is controlled so that the reaction mass is maintained at a temperature in the range from about 50° C. to about 120° C., and more preferably in the range from about 50° C. to about 95° C. at a pressure in the range from about 5 psig to about 25 psig.

The chlorine is deliberately "doctored" with oxygen present in the range from about 0.1% to about 1% by wt of the combined flow of ethylene, chlorine and oxygen, to increase the selectivity to EDC, and to inhibit the free radical reactions which produce triane and other polychlorinated compounds having more than two Cl atoms in each molecule. Though such polychlorinated compounds are undesirable, they are nevertheless unavoidably formed as byproducts of the reaction, but being higher boiling than EDC, tend to concentrate in the liquid reaction medium. Therefore, a bottoms stream 13 is withdrawn from the reactor. The oxygen is conveniently introduced by injecting air into either the ethylene or the chlorine feed lines, or into a separate sparger. This injection of air introduces a relatively large amount of nitrogen, comparable in volume to the amount of excess ethylene present in the effluent, which nitrogen simply "rides through" the system. The presence of this oxygen, though beneficial for the reaction producing EDC exacerbates the corrosion caused by unreacted chlorine and moisture.

The chlorine feed, whether liquid or gas, is not dry, for one reason or the other. Typically the moisture is present because the chlorine is derived from electrolytic cells. The level of moisture varies, ranging from about 20 parts per million (ppm) to about 1% by wt of the chlorine, more likely in the range from about 50 ppm to about 300 ppm. In addition to this water coming into the reactor with the chlorine, a lesser amount in the range from 1 ppm to about 50 ppm may come in with the ethylene, depending upon the source from which it is supplied. Further, a small amount of water may be generated by side reactions in the reactor. All the water introduced is distributed, when it leaves the reactor, between the overhead effluent leaving the reactor near its top, through line 14, and the bottoms line 13.

The effluent in line 14 is led into a product column 20 near its bottom. The product column is a distillation column fitted with trays or other conventional vapor-liquid equilibria staging means (not shown). A portion of the bottoms from the product column is recycled to the reactor 10 through a recycle line 21 by a recycle pump (not shown), the remainder being withdrawn through bottoms line 22.

The overhead of the product column 20 leaves through overhead line 23, is cooled in a condenser 30 by heat exchange with a cooling water stream indicated by the symbol CW, and commercially pure liquid EDC (99.5+%) flows through line 24 and is collected in condensate tank 40. This product EDC is withdrawn through line 25, a portion being refluxed through line 26 to near the top of the product column, the remainder being pumped through line 27 to product storage.

Not condensed in the condenser 30 are the light gases, namely ethylene, nitrogen, chlorine, HCl, oxygen, and minor amounts of water and EDC which are vented from the condenser as a condenser vent stream 31. A similar stream of uncondensed gases, the composition of which, like that of the condenser vent stream, is determined by the equilibrium conditions in the tank 40, comes off the tank. The tank vent stream leaves through line 41 and is combined with the condenser vent stream 31 in a product column vent stream line 42.

It is critical that the water content of the product column vent stream be less than 1.5% by wt of the product column vent stream, because this vent stream is to be chilled to a temperature low enough to freeze the water which, if present in a greater amount, will plug lines when it freezes. It is preferred to monitor the moisture content of the chlorine feed to ensure that the water content of the product column vent stream is less than 800 ppm.

It will be appreciated that, since the product column vent stream is to be chilled, the product column is operated with as low a top tray temperature as the temperature of an available cooling fluid stream for the condenser will allow, without losing too much ethylene which dissolves in the EDC condensate. In summer conditions, the temperature of the vent stream will preferably be in the range from about 100°-130° F., being dictated by summer cooling water temperature; in winter, the temperature of the vent stream may be as low as about 70°-90° F., again being dictated by the temperature of the water available.

The product column vent stream which is the combined flow from lines 31 and 41 into line 42, is preferably cooled in two stages. In the best embodiment, it is led into a brine condenser 45 where it is cooled by a cold brine stream identified as "brine", at a temperature within the range from about −30° F. to about 0° F. so that the major portion of the EDC and water in equilibrium with it, is condensed and leaves the condenser through line 46 at a temperature in the range from about 20°-60° F., more preferably in the range from about 30°-50° F.

In a second condensing stage, uncondensed gases from the brine condenser 45 are led through line 47 into HCl condenser 50 where they are cooled by a cold HCl stream identified as "HCl", at a temperature within the range from about −160° F. to about −140° F. so that, again, the major portion of the EDC, and water in equilibrium with it, is condensed and, mixed with uncondensed nitrogen, ethylene, HCl and oxygen ("non-condensables"), leaves the HCl condenser through line 51 at a temperature in the range from about −60° F. to about −10° F., more preferably in the range from about −30° to −10° F.

The condensate from the HCl condenser flows into a vent knock-out pot 52 where the liquid condensate is separated from the non-condensables which leave the knock-out pot 52 through line 53. The liquid condensate flows through line 54 and is combined with the liquid in line 46, the combined flow through line 55 being pumped by a pump (not shown) to the oxychlorination section of the EDC facility, to the "oxy wash train" where EDC is purified.

The non-condensables at about atmospheric pressure or slightly above, in the range from about 1-10 psig, in line 53 are led through line 57 to the suction of a vent compressor 60 and the compressor raises the pressure sufficiently to supply them to the oxy reactor, preferably in the range from 50-150 psig, through line 61. Line 56 is provided to lead the non-condensables to an incinerator when the vent compressor is shut down, or if desired, a portion of the non-condensables may be burned for fuel value.

The ranges of concentration of each of the components of a typical product column vent gas are as follows:

| Component | % by volume |
|---|---|
| Ethylene | 30-50 |
| Nitrogen | 30-40 |
| HCl | 5-8 |
| Oxygen | 3-5 |
| EDC | 2-4 |
| Ethane | 0.1-1. |
| Chlorine (ppm) | 300-2000 |
| Water (ppm) | 100-1500 |

Most preferred is a product column vent gas having the following average analysis:

| Component | % by volume |
|---|---|
| Ethylene | 46 |
| Nitrogen | 36 |
| HCl | 6.7 |
| Oxygen | 4.6 |
| EDC | 2.6 |
| Ethane | 0.6 |
| Chlorine (ppm) | 1000 |
| Water (ppm) | 500 |

I claim:

1. A process for minimizing corrosion due to moisture in vent gases from a high temperature direct chlorination reactor for converting ethylene to 1,2-dichloroethane, which vent gases are then utilized in an oxychlorination process, also for the production of 1,2-dichloroethane, said process comprising,
   (a) reacting wet chlorine, having a moisture content in the range from 100 ppm to about 1% by weight of the chlorine fed, with an excess over stoichiometric of ethylene in a liquid chlorohydrocarbon medium at a temperature of at least about 50° C. at atmospheric pressure or above, to yield product 1,2-dichloroethane in a draw-off from the reactor,
   (b) separating product 1,2-dichloroethane from higher boiling components in said draw-off from the reactor, in a product column,
   (c) condensing overhead from said product column in a condenser so as to condense the major portion of the 1,2-dichloroethane, from which condenser the 1,2-dichloroethane flows into an overhead drum, and vent a product column vent stream consisting essentially of nitrogen, ethylene, chlorine, 5 to 8% by volume of HCl and less than 1.5% by wt of water, based on the volume and weight respectively of the product column vent stream,
   (d) cooling the product column vent stream to a temperature in the range from about −30° C. to 0° C. in a condenser to condense condensables including water in the product column vent stream,
   (e) separating said water and condensables from non-condensables including nitrogen, chlorine, ethylene and HCl, without plugging lines with ice, and,
   (f) utilizing said non-condensables essentially free of water in said oxychlorination process, whereby corrosion due to the presence of water is minimized.

2. The process of claim 1 wherein said reactor is a boiling reactor operating at a pressure in the range from about atmospheric to about 25 psig, and said draw-off is vapor overhead effluent from the reactor.

3. The process of claim 1 wherein said reactor is a non-boiling reactor operating at a pressure in the range from about atmospheric to about 200 psig, and said draw-off is a liquid side stream from the reactor.

4. The process of claim 1 wherein said water in said product column vent stream is less than 800 ppm.

5. The process of claim 4 wherein said product column vent stream includes the combined non-condensable overhead gases from an overhead condenser and from an overhead condensate drum at a temperature in the range from about 70° F. to about 130° F., and said vent stream is condensed in two stages, a first stage from which non-condensables leave at a temperature in the range from about 20° F. to about 60° F., and a second stage from which non-condensables leave at a temperature in the range from about −60° to about −10° F.

* * * * *